United States Patent [19]

Schneider

[11] 4,282,626
[45] Aug. 11, 1981

[54] CLEANING DEVICES

[75] Inventor: Horst W. Schneider, West Covina, Calif.

[73] Assignee: California Institute of Technology, Pasadena, Calif.

[21] Appl. No.: 64,137

[22] Filed: Aug. 6, 1979

Related U.S. Application Data

[62] Division of Ser. No. 842,417, Oct. 17, 1977, Pat. No. 4,197,610.

[51] Int. Cl.$^3$ .............................................. A47L 7/00
[52] U.S. Cl. ...................................... 15/320; 15/322
[58] Field of Search .................. 15/320, 321, 322, 420

[56] References Cited

U.S. PATENT DOCUMENTS

| 2,293,115 | 8/1942 | Child | 15/322 |
| 3,243,830 | 4/1966 | Conrad | 15/420 X |
| 3,345,672 | 10/1967 | Lamers et al. | 15/322 |

FOREIGN PATENT DOCUMENTS 584806 10/1959 Canada ................................... 15/321

*Primary Examiner*—Chris K. Moore
*Attorney, Agent, or Firm*—Freilich, Hornbaker, Wasserman, Rosen & Fernandez

[57] ABSTRACT

Cleaning devices are described which include a vacuum cleaner nozzle with a sharp rim for directing incoming air down against the floor; a vacuum cleaner wherein electrostatically charged brushes that brush dirt off a floor, are electrically grounded to remove charges that could tend to hold dirt to the brushes; a vacuum cleaner head having slots that form a pair of counter-rotating vortices, and that includes an outlet that blows a stream of air at the floor region which lies between the vortices; a cleaning device that sweeps a group of brushes against the ground along a first direction, and then sweeps them along the same ground area but in a second direction angled from the first by an amount such as 90°, to sweep up particles lying in crevices extending along any direction; a device that gently cleans a surface to remove bacteria for analysis, including an inclined wall along which cleaning fluid flows onto the surface, a vacuum chamber for drawing in the cleaning fluid, and a dividing wall spaced slightly from the surface to separate the fluid source from the vacuum cleaner chamber; and a device for providing pulses of pressured air including a chamber to which pressured air is supplied, a ball that circulates around the chamber to repeatedly close an outlet, and an air source that directs air circumferentially to move the ball around the chamber.

3 Claims, 15 Drawing Figures

CLEANING DEVICES

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

This is a division of application Ser. No. 842,417, filed Oct. 17, 1977, now U.S. Pat. No. 4,197,610, issued Apr. 15, 1980.

BACKGROUND OF THE INVENTION

This invention relates to devices for cleaning surfaces.

Cleaning devices such as typical vacuum cleaners, rely upon motors of sufficient size to produce a large inflow of air through the vacuum cleaner head to create adequate pickup of dirt. Revolving brushes are utilized to loosen lint to be drawn into the vacuum head, but few other techniques are utilized to reduce the required power and improve dirt pickup.

SUMMARY OF THE INVENTION

In accordance with the present invention, various techniques are utilized to enhance the cleaning capability of cleaning devices. A simple vacuum cleaner head of the type which utilizes brushes to space the vacuum inlet from the surface to be cleaned, is formed with a housing having a sharply angled lower rim, which deflects incoming air down towards the rug to more effectively pick up dirt particles therefrom.

A vacuum cleaner head can be provided with slots on either side thereof which cause incoming air to swirl, so as to form a pair of vortices that rotate in opposite directions. A pressured air outlet directed at the floor area lying between and vortices, can help to dislodge dirt and at the same time help in the generation of the vortices.

In those situations where the surface to be cleaned may have cracks extending in many directions, a cleaner device is provided wherein the brushes brush in different directions over the same surface area to clean out dirt from any crevice. This can be accomplished by brushes that rotate about a first axis on a first frame, and wherein the first frame is rotatably mounted about a second axis on a second frame, and with the first and second axes perpendicular.

In those circumstances where an electrostatically charged brush can more effectively pick up dirt particles, a device is provided which discharges the brushes while also shaking them and applying a vacuum to them, to effectively draw off the dirt from the brushes.

In a device utilized for gently cleaning a surface, as wherein bacteria on a surface must be gently picked up for later observation, a cleaning device includes a chamber divided into two regions by a dividing wall. Cleaning fluid flows down an inclined wall in one region, under the dividing wall, and then into a vacuum-caused vortex leading to a vacuum pipe.

A device for aiding in the dislodging of dirt particles by providing air pulses, includes a circular chamber with an inlet at the hub for receiving high pressure air and an outlet at the periphery for delivering the air, a ball that circulates around the chamber to repeatedly close the outlet, and a control inlet which directs pressured air in a circumferential direction to control the rate of revolution of the ball.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
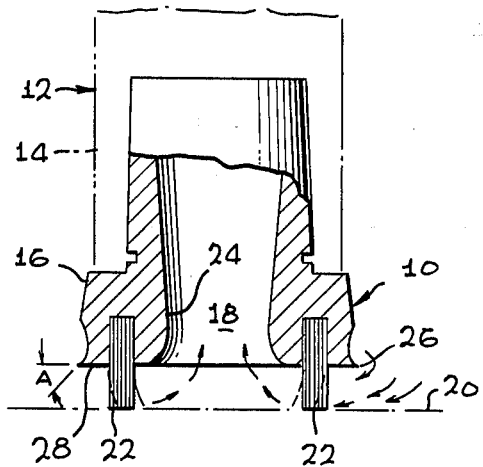
FIG. 1 is a sectional side view of a vacuum cleaner head constructed in accordance with one embodiment of the present invention, which utilizes a sharp rim to direct air downwardly.
Figure 2:
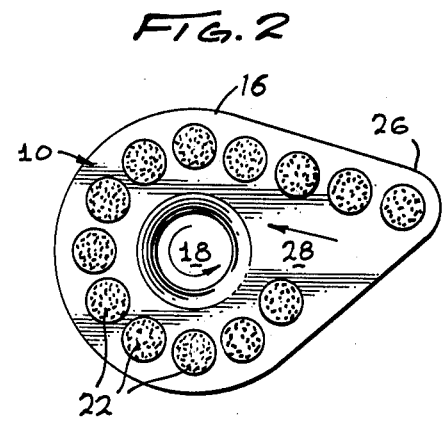
FIG. 2 is a bottom view of the head of FIG. 1.

FIGS. 1 and 2 illustrate a vacuum cleaner head 10 which is designed to be connected to a vacuum source 12 that includes a turbine pump (not shown) and a pipe 14 that connects the pump to the head. The head includes a hollow housing 16 having an end with an opening 18 for facing a floor 20 or other surface to be cleaned, to apply a vacuum thereto that draws the dirt. A group of brushes 22 are spaced about the opening to space the housing from the floor, as well as to help dislodge dirt therefrom. When a vacuum is applied through a passageway 24 of the housing to the open end 18, air passes between the brushes 22 and between the bristles of the brushes, to pick up dirt that is to be drawn into a bag or the like.

In accordance with the invention, a lower periphery of the housing at 26, which lies at the end of the housing nearest the opening 18, is formed at an acute angle A, with one surface 28 thereof substantially horizontal. The acute angle forces incoming air downwardly towards the surface 20 being cleaned, so that much of the incoming air will sweep close to the floor where most of the dirt and dust is lying which must be picked up with the air stream. In prior art vacuum cleaner heads, the bottom of the housing was rounded or formed substantially at a 90° angle with the bottom surface of the housing. A housing with a right angle rim allows air to flow thereunder nearly uniformly along the height of the brushes, so that much of the inflowing air does not flow close to the floor where most of the dirt is located. By forming the lower housing rim at an acute angle which is preferably at least a few degrees less than 90°, such as at an angle of 45° and which is preferably sharp, incoming air is directed largely down towards the floor, so that dirt is more efficiently entrained in the housing air stream. The brushes 22 are preferably relatively stiff to keep the housing opening a designed distance above the surface 20 to be cleaned, and the brushes are preferably only slightly impervious to air flow and close together, so that flow across the brushes occurs with high velocity and large turbulence, to thereby enhance the entrainment of dirt particles. The conduit 24 of the brush is preferably formed as a venturi to minimize the resistance to inflow of air.

As shown in FIG. 2, the housing 16 can be formed with a nose portion 26 extending radially outward and with its sides generally formed at an angle of less than 90° to enable the cleaning of corner areas. Also, the brushes are arranged in a spiral, and with a gap 28 at the end of the spiral arrangement to permit the entry of air in a circumferential direction to create a vortex.

Figure 2A:
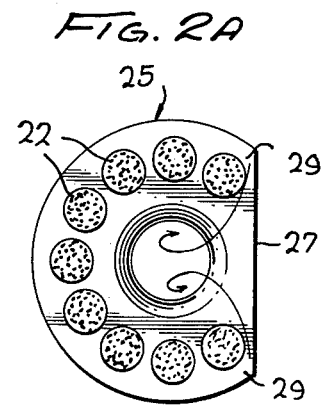
FIG. 2A is a bottom view of a vacuum cleaner head constructed in accordance with another embodiment of the invention.

The brush of FIG. 2 can be modified to the horse shoe shape of the brush 28 FIG. 2A, to enable the cleaning of molding extending along the bottom of a side wall of a room. The flat side 27 can be placed along a straight surface, such as a building, so that air enters at the end 29 of the gap in the brushes, to create counter rotating vortexes.

Figure 3:
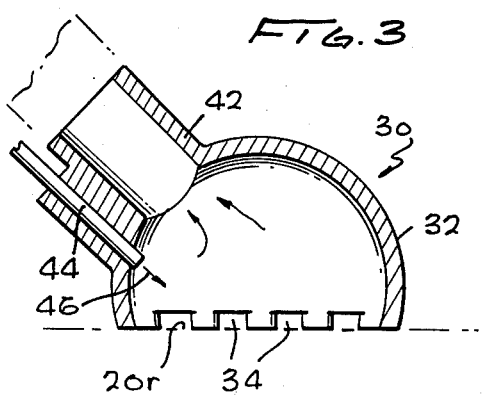
FIG. 3 is a sectional side view of a vacuum cleaner head constructed in accordance with another embodiment of the invention, wherein slots formed in the head create two counter rotating vortices, and air is discharged at the floor region lying between the vortices.
Figure 4:
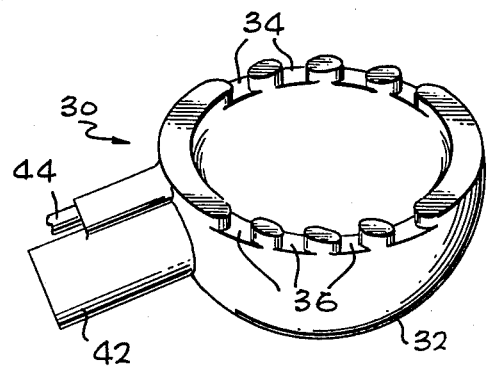
FIG. 4 is a bottom perspective view of the head of FIG. 3.
Figure 5:
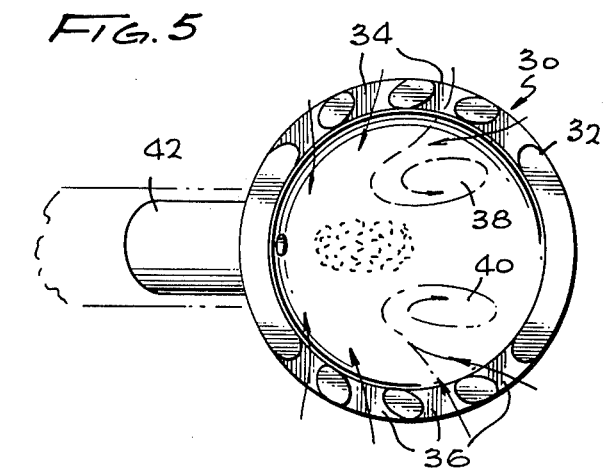
FIG. 5 is a bottom view of the head of FIG. 3, showing the manner in which it creates vortices.

FIGS. 3–5 illustrate a vacuum cleaner head 30 which includes a housing 32 formed with groups of slots 34, 36 on opposite sides of the bottom portion of the head. Each group of slots is formed to urge incoming air to swirl to form a vortex, and with the two groups of slots 34, 36 oriented to form two vortices 38, 40 that swirl in opposite directions, the vortex 38 turning counter clockwise while the vortex 40 turns clockwise. While a vacuum is applied to the housing through an inlet 42, high pressure air is also applied through conduit 44, to blow a stream of air at the region of the floor 20r that lies between the two vortices 38, 40. The stream of air, as indicated by arrow 46, encourages the two vortices 38, 40 to swirl faster, to more effectively entrain dust and carry it through the vacuum inlet 42. The high pressure air delivered through the conduit 44 also helps dislodge dirt from the floor, to allow it to be entrained in the vortices. Thus, by providing groups of slots 34, 36 that encourage the formation of two counterrotating vortices, and by blowing high pressure air between the vortices to increase their speed, as well as to help dislodge dirt from the floor, more effective pickup of dirt is achieved.

Figure 6:
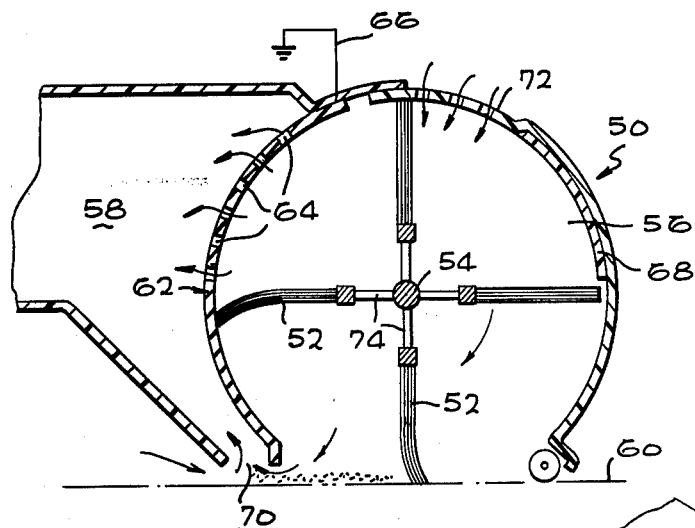
FIG. 6 is a sectional side view of a vacuum cleaner head constructed in accordance with another embodiment of the invention, wherein electrostatically charged brushes are electrically grounded at the time when they are shaken and a vacuum is applied thereto.
Figure 7:
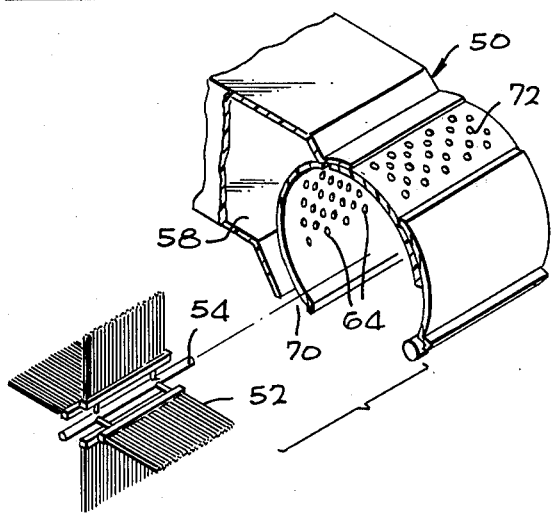
FIG. 7 is an exploded perspective view of the head of FIG. 6.

FIGS. 6 and 7 illustrate another vacuum cleaner apparatus 50 which utilizes voltages applied to brushes 52 that sweep along the ground, to enable the brushes to pick up dirt and then to enable the dirt to easily leave the brushes. Rows of brushes 52 are mounted on a shaft 54 which is rotated by a motor (not shown). The brushes rotate within a chamber 56 which is substantially at ambient pressure, but through which air flows in reaching a vacuum conduit 58. As the brushes rotate against a surface 60 to be cleaned, the brushes can pick up an electrostatic charge which is useful in attracting fine dirt particles to the brush. However, if steps were not taken to dislodge the electrostatically held particles, then they would remain on the brush to recontaminate the swept surface. To minimize such recontamination, a curved shield 62 is provided against which the brushes brush after lifting off the ground.

The curved shield 62 has numerous staggered holes 64 communicating with the vacuum conduit 58 to enable air flow to remove particles. In addition, the shield 62, which is constructed of metal to make it electrically conductive, is connected by a wire 66 to an electrical ground. As the brushes sweep across the shield, the electrostatic charges on their tips are largely removed, so that small dirt particles that tend to cling thereto are set free, and can be drawn into the air stream passing into the vacuum conduit 58. It may be noted that the holes 64 in the shield help to beat the brushes rotating thereagainst to further aid in shaking loose dust.

In order to increase dirt pickup, an electrically non-conductive element 68 of material such as hard rubber, can be provided to contact the tips of the brushes prior to their sweeping against the ground, to electrostatically charge the brush tips so as to better attract small dust particles which will be later released when the brush tips are discharged. It may be noted that the rotating brush can tend to sweep some of the dirt rearwardly, and therefore the vacuum conduit is formed with an opening 70 located immediately behind the brushes which brush towards the opening, to pick up rearwardly brushes dirt. The upper end of the vacuum cleaner housing at 72 is provided with numerous holes, to enable the inflow of air that will pass partially through the holes 64 in the grounding shield 62, and part of which will pass with rearwardly-swept dirt into the opening 70. There are also slots 74 in the brush assemblies to minimize pressure difference on opposite sides of each brush to avoid undesired bending.

Figure 8:
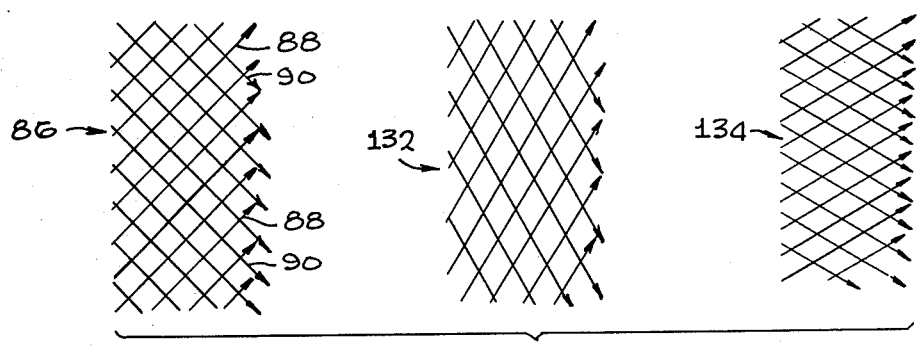
FIG. 8 contains three diagramatic views of sweep patterns that can be utlized to clean a surface.
Figure 9:
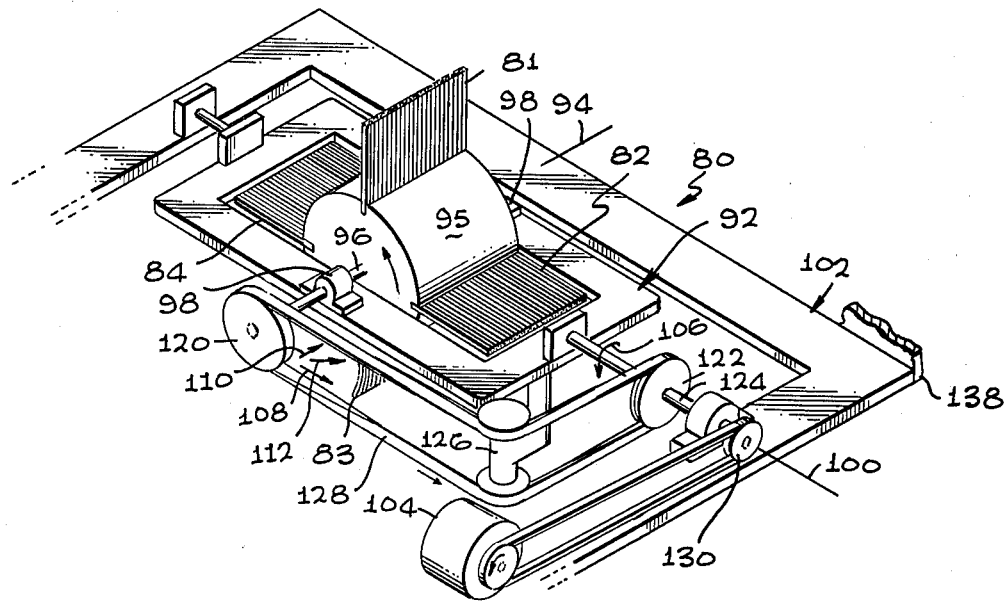
FIG. 9 is a perspective view of a sweeping apparatus which can create the sweep patterns of FIG. 8.

FIG. 9 illustrates a cleaning apparatus 80 with brushes 81–84 that can dislodge particles lying in small scratches on a surface such as the surface of a metal sheet. Most rotating brushes sweep across a surface in one direction, which is not effective in removing particles lying in a scratch that extends largely perpendicular to the direcraton of sweeping. The apparatus of FIG. 9 can sweep the brushes in the pattern shown at 86 in FIG. 8, wherein the brushes first sweep in one direction indicated by arrow 88, and then sweep over the same surface area in the direction indicated by arrows 90 which are angled by more than a few degrees from the arrows 88. In the sweep pattern 86, the directions 88 and 90 are perpendicular to each other.

In the apparatus 80, the brushes 81–88 are rotatably mounted with respect to a first frame 92 about an axis 94. This is accomplished by mounting the inner ends of the brushes to a member 95 that is fixed to a shaft 96 that rotates in bearings 98 on the first frame 92. The first frame 92 is rotatably mounted about an axis 100 on a second frame 102, with the axis 100 being substantially perpendicular to the axis 94. A motor 104 rotates the first frame 92 about the second one 102, and also rotates the brushes 81 about the axis 94.

Figure 9A:
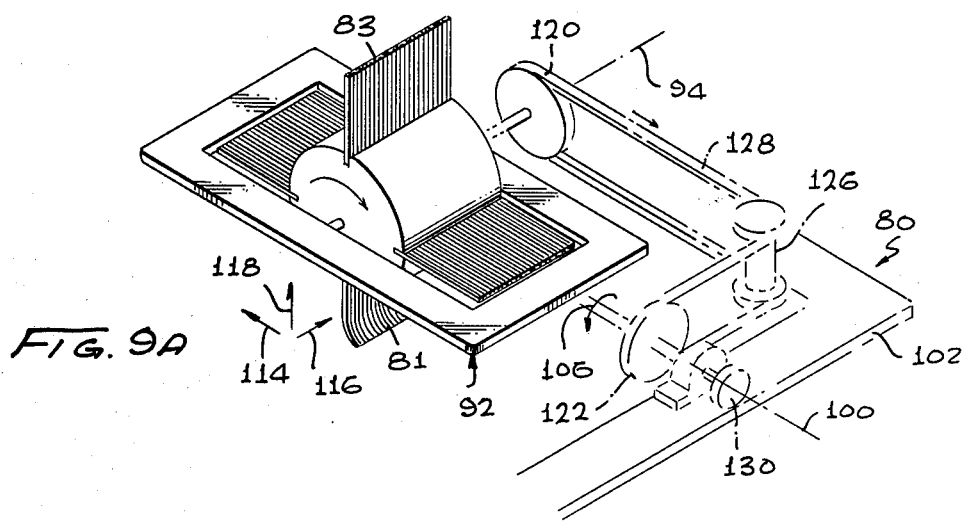
FIG. 9A is a partial perspective view of the apparatus of FIG. 9, but rotated about 180° from the position of FIG. 9.

The manner in which the cleaning apparatus 80 causes the brushes to sweep in opposite directions over the same floor area, can be best understood by considering the apparatus of FIG. 9 after the first frame 92 has rotated 180° to the position illustrated in FIG. 9A. In FIG. 9, the first frame rotates in the direction indicated by arrow 106, which results in the brush 83 tending to sweep across the ground in the direction of arrow 108. However, since the brush 83 is also moving in the direction of arrow 110 due to rotation of the first frame about the axis 100, the brush 83 is actually moving in the direction of arrow 112 which is the sum of the vectors indicated by arrows 108 and 110.

FIG. 9A illustrates the cleaning apparatus after the first frame 92 has turned by 180° from the orientation of FIG. 9. In FIG. 9A, brush 81 is in contact with the ground. The rotation of the brushes about axis 94, tends to sweep the brush 81 in the direction to arrow 114. However, at the same time the first frame is rotating about the axis 100 which causes the brush 81 to also move in the direction of arrow 116. The combination of the vectors represented by arrows 114 and 116 is the vector 118, which represents movement of the brush 81 in the direction 118. The direction 118 is angled 90° from the direction of the arrow 112 of FIG. 9 which is the direction in which the brush 83 swept across the ground. Thus, with the apparatus 80 stationary or moving slowly along the ground as compared to the speed of rotation of the brushes and first frame, the brushes sweep alternately in perpendicular directions across every area of the ground which is swept, in the pattern indicated at 86 in FIG. 8.

The mechanism for rotating the first frame 92 about axis 100 on the second frame, and for rotating the brushes on member 94 about axis 94 with respect to the first frame, includes a first pulley 120 fixed to the shaft 96 that lies on axis 94, a second pulley 122 which lies on a shaft 124 extending along axis 100 and connecting the first and second frames, and an idler device 126. A belt 128 extends around the two pulleys 120, 122 and around a pair of idler pulleys on the idler device 126. The motor 104 turns another pulley 130 which is fixed with respect to the pulley 122. If the pulleys 120, 122 are the same size, so that the brush-holding member 94 rotates at the same angular velocity about each of the two axes 94, 100, then the brushes will sweep in the pattern illustrated at 86 in FIG. 8 wherein the two directions of sweeping indicated by arrows 88 and 90 are perpendicular to one another.

Sweeping patterns other than that shown at 86 can be obtained, such as those illustrated at 132 and 134 in FIG. 8, wherein the directions of sweep are angled by more than 90° and less than 90°, respectively from one another. If the pulley 122 is smaller than the pulley 120, so that the brushes rotate more rapidly about the axis 100, than the pattern illustrated at 134 will be effected, wherein the directions of sweeping are more closely parallel than the perpendicular pattern at 86. On the other hand, if the pulley 122 is made larger than the pulley 120, then a sweep pattern of the type illustrated at 132 will be obtained. If a gear drive is utilized, a corresponding difference in gear sizes can be used.

It is normally desirable to angle the two directions of sweep by at least 45° and less than 135° from each other, so that there are large sweep components along the direction of cracks that extend in any direction. Walls 138 forming an enclosure, are preferably provided around the sweeping brushes together with a vacuum source, to pick up dirt-dislodged by the brushes.

Figure 10:
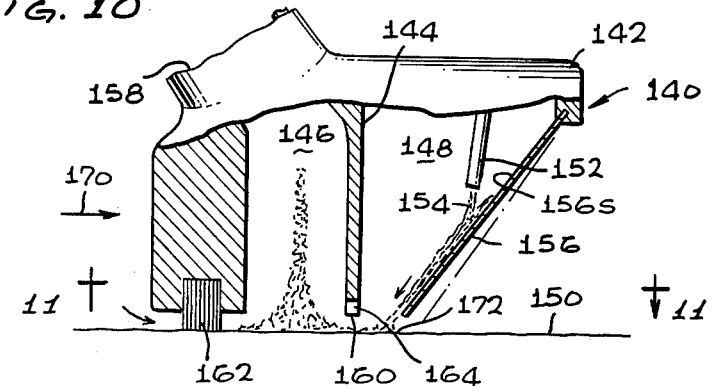
FIG. 10 is a sectional side view of a vacuum cleaner head constructed in accordance with another embodiment of the invention, which gently cleans material from a surface by the use of gently applied cleaning fluid.
Figure 11:
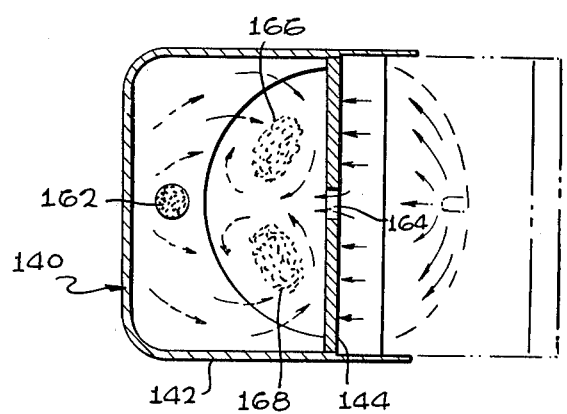
FIG. 11 is a view taken on the line 11–11 of FIG. 10.

FIGS. 10 and 11 illustrate another cleaning apparatus which is especially useful for cleaning biological samples from a surface without damaging them, to enable later analysis and to also leave the clean surface extremely clean. The cleaning apparatus 140 includes a housing 142 forming a hollow space, and a dividing wall 144 dividing the space into two hollow regions 146, 148. The lower ends of the hollow regions which face the surface 150 to be cleaned, are open. The apparatus also includes a nozzle 152 which applies a liquid cleaning fluid 154 such as water with detergent, to an inclined wall 156 which forms one wall of the hollow region 148. The other hollow region 146 is coupled to a vacuum conduit 158 that is connected to a vacuum pump (not shown) that applies a vacuum thereto. The nozzle 152 applies a metered amount of liquid 154 to the inclined surface 156s of the inclined wall so that the liquid spreads out into a thin film.

The film of cleaning fluid moves down against the surface 150 to be cleaned, and under the dividing wall 144 whose lower end 160 is slightly spaced from the surface to be cleaned. The film then moves into the vacuum chamber region 146 where the fluid is drawn up with air into the vacuum conduit 158. A spacer 162 spaces the vacuum region 148 and the rest of the housing slightly from the surface 150 to be cleaned, so that air flows from the outside of the housing around the spacer 162 to help form a vortex of incoming air that aids in the pickup of the cleaning fluid. The dividing wall 144 is also formed with an inlet 164 lying sufficiently above the liquid film on the surface, to allow the inflow of air thereto, to encourage the formation of a pair of vortices at 166, 168 in somewhat the same manner as that shown in FIG. 5.

The cleaning apparatus 140 can be moved over a surface in the direction of arrow 170, so that after liquid is applied to the surface to detach dirt (including micro organisms), air flowing around the spacer 162 dries the surface. Thus, the device applies a cleaning liquid to the surface which can aid in sweeping away particles as well as entrap and dissolve them, so that particles clinging tenaciously to the surface, as well as oily and film-like contaminants, can be removed. A handheld prototype device constructed in the manner illustrated in FIGS. 10 and 11, has been constructed and been found to remove as much as 90 to 98% of micro-organisms and particulate as small as 5 microns in a sweep over a relatively smooth hard surface. The inclined wall 156 is relatively thin so that it can vibrate, and the frequency can be varied by changing the thickness and cantilevered length at the wall. Such vibrations are helpful, because it is found that the point 172, where the cleaning fluid initially contacts surface 150, is where the removal efficiency of the cleaning fluid is greatest; the rapid back and forth movement of this point causes repeated sweeping over a small surface area to further increase the cleaning efficiency.

Figure 12:
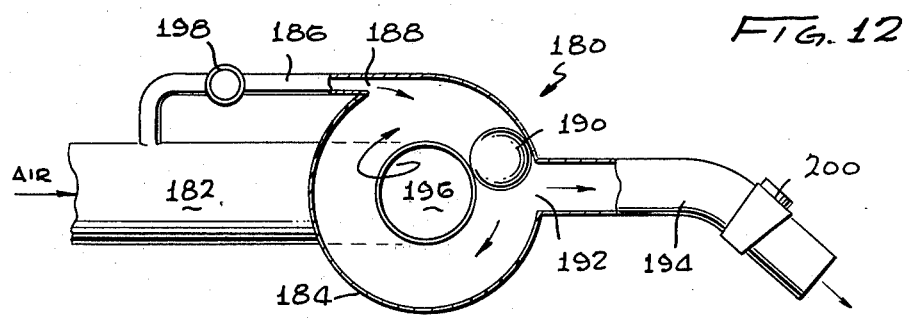
FIG. 12 is a simplified sectional view of a pulsing air source device, constructed in accordance with another embodiment of the invention.
Figure 13:
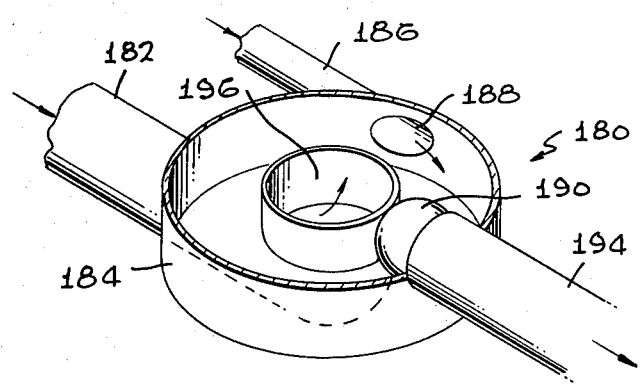
FIG. 13 is a partial perspective view of the device of FIG. 12.

FIGS. 12 and 13 illustrate a cleaning apparatus 180 which can produce a pulsed stream of high pressure air for blowing away dirt, or for other purposes. A common method of cleaning an object, particularly in a machine shop where pressured air is readily available, is to direct a stream of compressed air against the object to blow away unwanted material. However, when a steady stream of compressed air is directed against the surface, a boundary layer is generated along the surface, where air moves at a much lower velocity than the free air stream, and this boundary layer is inefficient in dislodging particles. By utilizing pulses of air, the boundary layer is repeatedly interrupted, so that cleaning is more efficiently accomplished.

In the cleaning device 180, high pressure air is supplied through an inlet pipe 182 which is connected to the center of a circular chamber 184. In addition, a control conduit 186 is provided which delivers a small amount of the air in pipe 182 to the chamber through an inlet 188 which directs the air in a circumferential direction. A ball 190 is loosely disposed in the circular, or ring-shaped chamber 184, to circulate thereabout and repeatedly close an outlet 192 which leads to an outlet pipe 194 through which pulses of compressed air are to be applied. The compressed air entering through the control outlet 188 produces a circulating air flow that moves the ball around the chamber, so that the air which would normally move from a main inlet port 196 to the outlet 192 is repeatedly interrupted. In this way, the air passing along the outlet pipe 194 is repeatedly interrupted, so that when the device is used to blow away particles on a surface, the boundary layer of air on the surface is repeatedly interrupted.

A control valve 198 may be provided along the control conduit 186 to limit the amount of air passing therealong, to thereby control the rotational speed of the ball 190 and therefore the frequency at which the air pulses are produced. A shut-off valve 200 can also be provided along the outlet pipe to enable the shut-off of air 12. The entire pulsing device 180 can be formed as part of a handpiece for connection to a flexible air hose, so that it can be utilized by a person in a machine shop to blow away chips from a part.

Thus, the invention provides cleaning devices that can be utilized to clean dirt from a surface. The devices provide efficient vacuum cleaner heads, sweeping devices, cleaning and biological sampling devices, and air pulsing devices.

Although particular embodiments of the invention have been described and illustrated herein, it is recognized that modifications and variations may readily occur to those skilled in the art, and consequently, it is intended that the claims be interpreted to cover such modifications and equivalents.

I claim:

1. Apparatus for applying a liquid to a surface comprising:
  a housing having walls forming a hollow space and a wall dividing said space into two hollow regions with open lower ends for facing the surface;
  means for applying a vacuum to a first of said regions;
  means for slightly spacing at least a lower end of said dividing wall slightly from the surface when the housing assumes a predetermined upright position with respect to the surface; and
  means for applying a fluid to a predetermined wall of a second of said hollow regions which is spaced from said dividing wall, said predetermined wall being inclined so that progressively lower portions thereof are progressively closer to said dividing wall, and said dividing wall being easily deflected and resilient so it can vibrate.

2. Apparatus for applying a liquid to a surface comprising:
  a housing having walls forming a hollow space and a wall dividing said space into two hollow regions with open lower ends for facing the surface;
  means for applying a vacuum to a first of said regions;
  means for applying a fluid to a predetermined wall of a second of said hollow regions which is spaced from said dividing wall; and
  means for slightly spacing at least a portion of said walls of said housing from the surface when the housing assumes a predetermined upright position with respect to the surface;
  said wall dividing said hollow space into two hollow regions has an opening of a width much less than half the width of said hollow regions, to produce a localized large flow of air from said second hollow region into said first hollow region; and
  said means for spacing includes a member located on a side of said first hollow region opposite said opening in said dividing wall, to block free air flow thereby, whereby to create counter-rotating vortices in the first hollow region.

3. Apparatus for applying a liquid to a surface comprising:
  a housing having walls forming a hollow space and a wall dividing said space into two hollow regions with open lower ends for facing the surface;
  means for applying a vacuum to a first of said regions;
  means for applying a fluid to a predetermined wall of a second of said hollow regions which is spaced from said dividing wall; and
  means for slightly spacing at least a portion of said walls of said housing from the surface when the housing assumes a predetermined upright position with respect to the surface, to allow the inflow of air;
  said fluid applying means being constructed to apply fluid to said predetermined wall primarily at locations thereon spaced from said surface, so that fluid can run down said wall onto said surface, and said spacing means spacing said dividing wall from said surface so fluid running down said predetermined wall can pass along said surface and under said dividing wall into said first hollow region.

* * * * *